United States Patent [19]
Hunt et al.

[11] Patent Number: 5,646,311
[45] Date of Patent: Jul. 8, 1997

[54] RECOVERY OF TOCOPHEROLS

[75] Inventors: Tracy K. Hunt, Kankakee, Ill.; Lutz Jeromin, Hilden, Germany; Wilhelm Johannisbauer, Erkrath, Germany; Bernhard Gutsche, Hilden, Germany; Volkmar Jordon, Mettman, Germany; Herbert Wogatzki, Duesseldorf, Germany

[73] Assignee: Henkel Corporation, Plymouth Meeting, Pa.

[21] Appl. No.: 654,483

[22] Filed: May 28, 1996

Related U.S. Application Data

[62] Division of Ser. No. 531,366, Sep. 20, 1995, which is a continuation of Ser. No. 180,592, Jan. 13, 1994, abandoned, which is a continuation of Ser. No. 103,628, Aug. 6, 1993, abandoned.

[51] Int. Cl.$^6$ .................... C07D 311/72; C07C 69/24
[52] U.S. Cl. ............................... 549/413; 554/175
[58] Field of Search ...................... 549/413; 554/175

[56] References Cited

U.S. PATENT DOCUMENTS

| | | | |
|---|---|---|---|
| 3,335,154 | 8/1967 | Smith | 549/413 |
| 4,594,437 | 6/1986 | Sampathkur | 549/413 |
| 5,190,618 | 3/1993 | Top et al. | 203/34 |

FOREIGN PATENT DOCUMENTS

| | | |
|---|---|---|
| 171009 | 7/1985 | European Pat. Off. |
| 610742 | 8/1994 | European Pat. Off. |
| 3126110 | 1/1982 | Germany. |
| 60-178883A | 9/1985 | Japan. |
| 60-185776A | 9/1985 | Japan. |
| 61-093178A | 5/1986 | Japan. |
| 1008767 | 5/1962 | United Kingdom. |
| 2145079 | 11/1986 | United Kingdom. |

OTHER PUBLICATIONS

*Encyclopedia of Chemical Technology*, vol. 9, Kirk–Othmer, editors, John Wiley & Sons, NY, NY, 1980, pp. 306–308.

"Crystallization", *Encylcopedia of Chemical Technology*, vol. 7, 3rd Edition, pp. 243–285, Kirk–Othmer, editors, John Wiley & Sons, NY, NY, 1971.

E. Stanford, "Evaporation," *Encyclopedia of Chemical Technology*, vol. 9, pp. 472–493 Kirk Othmer, editors, J.Wiley & Sons, NY, NY, 1980.

E. Hafslud, "Distillation", *Encyclopedia of Chemical Technology*, vol. 7, pp. 849–891, Kirk–Othmer, editors, J. Wiley & Sons, NY, NY, 1979.

"Catalysts, Polymer–Supported", *Encyclopedia of Polymer Science and Engineering*, vol. 2, pp. 708–729, J. Wiley & Sons, NY, NY, 1985.

*Handbook of Chemistry and Physics*, 55th Edtion, Robert C. Weast, Editor, CRC Press, Cleveland, Ohio, 1973, pp. E–56–58.

M. Chrysam, "Deodorization", *Bailey's Industrial Oil & Fat Products* vol. 3, T.H. Applewhite, Editor, John Wiley & Sons, New York, New York, pp. 127–165, 1980.

*Primary Examiner*—Nicky Chan
*Attorney, Agent, or Firm*—Ernest G. Szoke; Wayne C. Jaeschke; John Daniel Wood

[57] ABSTRACT

Starting from a mixture containing tocopherol, fats and/or fat derivatives, more particularly fatty acids, and optionally sterol and/or sterol derivatives, the free fatty acids present in the mixture are esterified with an alcohol. The mixture is then transesterified with an alcohol in the presence of a basic catalyst. After the transesterification, the excess lower alcohol is distilled off from the reaction mixture. The transesterification catalyst and the glycerol present, if any, are removed and the fatty acid alkyl ester is distilled off from the mixture. Distillation of fatty acid alkyl esters can be accomplished with a packed column in sequence with a wiped film evaporator. The simultaneous recovery of tocopherol and sterol is possible. Tocopherols and sterols can be separated by the crystallization of sterols from a blend of organic solvents.

18 Claims, No Drawings

RECOVERY OF TOCOPHEROLS

CROSS-REFERENCE TO RELATED APPLICATIONS

This application is a divisional application of U.S. Ser. No. 08/531,366, filed Sep. 20, 1995, which is a continuation of U.S. Ser. No. 08/180,592, filed Jan. 13, 1994, now abandoned, which is continuation of U.S. Ser. No. 08/103,628, filed Aug. 6, 1993, now abandoned.

FIELD OF THE INVENTION

This invention relates to a process for recovering tocopherol and, optionally, sterol from a mixture containing tocopherol, fats and/or fat derivatives, more particularly fatty acids, and optionally sterol and/or sterol derivatives.

Tocopherol compounds occur in many vegetable and animal oils and are also referred to as vitamin E. The vitamin E relates to the physiological effect of these food ingredients.

There are 8 naturally occurring substances with vitamin E activity. They are derivatives of 6-chromanol and belong to two groups of compounds. The first group is derived from tocol and carries a saturated isoprenoidal side chain containing 16 carbon atoms. This group includes alpha-, beta-, gamma-, and delta-tocopherol. The compounds differ in their degree of methylation at the benzene ring of the tocol. Alpha-tocopherol is the substance with the strongest biological vitamin E effect and the greatest technical and economical importance. It is the dominant tocopherol in human and animal tissue.

The second group of substances with vitamin E activity are the derivatives of tocotrienol. They differ from the other tocopherol homologs in the unsaturated isoprenoidal side chain containing 16 carbon atoms. The naturally occurring tocoenols also show vitamin E activity and are normally isolated from their natural sources together with the saturated tocopherol homologs in the recovery of vitamin E. In the context of the present invention, the name "tocopherol" is also intended to encompass these tocopherol homologs, i.e. tocopherol are found in vegetable oils, such as wheatgerm oil, corn oil, soybean oil and palm kernel oil. However, tocopherol is also found in other vegetable oils, for example in safflower oil, peanut oil, cottonseed oil, sunflower oil, rapeseed oil, palm oil and other vegetable oils.

The natural plant oils contain only small quantities of tocopherol. Concentration is undesirable for commercial applications. In addition, impurities are supposed to be removed to enhance the antioxidizing effect and vitamin E activity. Accordingly, the most important natural sources of tocopherol are not the vegetable oils themselves, but rather the steam distillates—also know as steamer distillates—obtained in the deodorization of vegetable and animal oils. Although the tocopherols are obtained in concentrated form, they are mixed with sterol and sterol esters, free fatty acids and triglycerides. The distillate from the deodorization of soybean oil is particularly interesting. The particular suitability of soybean oil as a source of tocopherols is mentioned, for example, in *Fat Sci. Techol.*, Vol. 91, 1989, pages 39 and 41 in a comparison of the deodorization distillates of soybean oil and rapeseed oil. The soybean oil steamer distillate contains approximately 10% (maximum) by weight mixed tocopherols and the same amount of sterols which are predominantly present in their ester form.

There are various known processes for the concentration of tocopherol, namely esterification, saponification and fractional extraction. Thus, according to DE 31 26 110 A1, tocopherol concentrates are obtained from secondary products of the deodorization of oils and fats by esterification of the free fatty acids present therein by addition of an alcohol or by removal of the free fatty acids from the distillates by distillation, after which these products are subjected to hydrogenation and subsequently to solvent fractionation to extract the tocopherols. Another process for concentrating tocopherol is known from the same document. In this process, the deodorization distillates are subjected to transesterification with methanol and the fatty acid methyl esters are distilled off. The residue is concentrated by molecular distillation.

In another process known from EP 171 009 A2, the tocopherol-containing material is contacted with a sufficient quantity of a polar organic solvent which dissolves the tocopherols, but not the impurities. The polar phase enriched with tocopherol is separated off and the tocopherol is recovered therefrom.

It is also known that the tocopherols can be separated by adsorption onto basic anion exchangers. This variant is possible if the mixture contains little, if any, fatty acid. The sterols, glycerides and other neutral or basic substances are not adsorbed (*Ulmanns Enzyklopädie der Technischen Chemie*, 4th Edition, Vol. 23, 1984, page 645).

It is also known that sterols can be separated from tocopherols by fractional crystallization after concentration. In this process, tocopherol passes into solution and sterol crystallizes out. Tocopherol and sterol can also be separated by distillation, except that in this case the sterol is at least partly destroyed. Accordingly, two useful products are obtained after the separation of tocopherol and sterol.

Known processes for the recovery of tocopherol and, optionally, sterol are attended by various disadvantages.

The extraction processes often have to be adapted to the starting mixture because the impurities present therein have a considerable bearing on extraction, and the desired useful products, tocopherol and sterol, do not always pass into the desired phase with the same extraction process and different starting mixtures. In addition, known extraction processes use physiologically unsafe solvents.

Ion exchangers have a specific effect on the starting material, required thorough preliminary purification of the mixture and do not allow tocopherol and sterol to be simultaneously concentrated.

In a variant described in DE 31 26 110 A1, tocopherol is subjected to molecular distillation or to steam distillation after esterification of the free acids with polyhydric alcohols in order to obtain a distillate having a high tocopherol content. However, the process step of molecular distillation is uneconomical on an industrial scale while steam distillation involves exposure to relatively high temperatures which at least partly destroys the sterols. In the latter case, therefore, only the thermally more stable tocopherol can be obtained in high yields.

Accordingly, the problem addressed by the present invention was to provide a process for the recovery of tocopherol and, optionally, sterol which would be applicable to many different starting mixtures and which would not use any toxicological or ecologically unsafe solvents, would not involve exposure to high temperatures, would give high yields and would be economically workable on an industrial scale. In addition, the simultaneous recovery of tocopherol and sterol would be possible.

SUMMARY OF THE INVENTION

This invention relates to various steps in the recovery of tocopherols, typically from sources in which the tocopherols are in a mixture additionally comprising fatty compounds (e.g. fatty acids and/or fatty glycerides) and sterols (e.g. free sterols and/or steryl fatty acid esters). The various steps of the processes of the invention can be outlined as follows. As will be appreciated, the following outline deals with two alternative pre-esterification/transesterification processes, followed by a distillation process (which serve to remove fatty compounds from the mixture, e.g. as lower alkyl fatty esters), and a crystallization process (which serves to separate sterols from tocopherols).

I. PRE-CONVERSION AND REMOVAL OF FATTY COMPOUNDS

A. Pre-esterification/Transesterification

1. Pre-Esterification/Transesterification with methanol recovery

In one aspect, this invention relates to a process for recovery of tocopherols from a mixture comprised of fatty acids and tocopherols, said process comprising:

pre-esterifying free fatty acids present in said mixture with a lower alcohol (preferably a member selected from the group consisting of primary and secondary mono-alkanols having less than five carbon atoms), transesterifying fatty acid esters present in said mixture with a lower alcohol in the presence of a basic catalyst, and distilling excess lower alcohol from the product of said transesterification (and preferably recycling at least a portion of said distilled methanol to said transesterifying step), washing the product of said transesterification (preferably with essentially pure water) to remove said basic catalyst and glycerol produced by said transesterification, distilling fatty acid alkyl esters from said mixture after inactivation (e.g. neutralization or removal) of said basic catalyst.

In preferred embodiments, the process additionally comprises one or more of the following steps of employing a polymer-supported acid catalyst in said pre-esterification and employing a mixture comprised of both one or more tocopherol compounds and one or more sterol compounds (preferably comprised of one or more sterol esters that are transesterified in the pre-esterification and/or said transesterification steps) and recovering from said mixture one or more tocopherol compounds separate from one or more sterol compounds after said distillation of fatty acid alkyl esters.

In a related aspect, this invention relates to a process comprising:

free fatty acids present in the mixture are esterified with a lower alcohol, preferably methanol, the mixture is subsequently transesterified with the lower alcohol in the presence of a basic catalyst, the excess lower alcohol is distilled off from the reaction mixture after the transesterification, the transesterification catalyst and optionally the glycerol present are removed, more particularly by washing, the fatty acid alkyl ester is distilled off from the mixture, more particularly after removal of the transesterification catalyst, and if desired, tocopherol and sterol are separated by methods known per se.

2. Pre-esterifying with Higher Alcohol (and Transesterifying with Lower Alcohol)

In another aspect, this invention relates to a process for recovery of tocopherols from a mixture comprised of fatty compounds and tocopherols, said process comprising:

pre-esterifying free fatty acids present in said mixture with a higher alcohol (preferably a member selected from the group consisting of primary and secondary mono-alkanols having at least five carbon atoms) and removing by-product water by volatilization thereof, transesterifying fatty acid esters present in said mixture with an alcohol, preferably a lower alkanol, in the presence of a basic catalyst, and distilling alkyl fatty acid esters from said mixture after incapacitation (e.g. neutralization or removal) of said basic catalyst.

In preferred embodiments, the process additionally comprises one or more of the following steps, preferably each of the following steps in the order set forth below:

employing a higher alcohol that is moderately volatile (and preferably essentially immiscible with water) such that a portion of said alcohol is distilled with said by-product water (and is preferably separated by gravity from said by-product water after condensation of said higher alcohol) and recycling higher alcohol after its distillation (and preferably after separation from by-product water), distilling excess lower alcohol from the product of said transesterification, washing the product of said transesterification to remove said basic catalyst and glycerol produced by said transesterification, distilling higher alcohol from the product of said transesterification as a fraction separate from said alkyl fatty acid esters, and employing a mixture comprised of both one or more tocopherol compounds and one or more sterol compounds (preferably comprised of one or more sterol esters that are transesterified in the pre-esterification and/or said transesterification steps, preferably at least 50% by weight of the sterol esters are converted to free sterols, more preferably at least about 80%, typically from about 85% to about 95%) and recovering from said mixture one or more a tocopherol compounds separate from one or more sterol compounds after said distillation of fatty acid alkyl esters.

B. Alkyl Fatty Ester Distillation

1. Distillation with Packed Column

In another aspect, this invention relates to an evaporative process for the separation of fatty acid lower alkyl esters from a mixture additionally comprising tocopherols and sterols, said process comprising:

introducing said mixture into a moderately heated zone of elevated temperature and reduced pressure, said zone containing multiple packing elements in an essentially continuous bed, said elevated temperature and reduced pressure being effective to provide within said continuous bed a first vapor phase enriched with respect to said mixture in alkyl fatty acid esters and a first liquid phase enriched with respect to said mixture in tocopherols and sterols;

removing liquid phase enriched in tocopherols and sterols from said continuous bed at a point gravitationally below the point of introduction of said mixture into said heated zone;

removing vapor phase enriched in alkyl fatty acid esters from said continuous bed at a point gravitationally above the point of introduction of said mixture into said heated zone;

applying said liquid phase enriched in tocopherols and sterols as a film to a highly heated surface in proximity with a zone of reduced vapor pressure to provide a second vapor phase enriched with respect to said liquid phase in alkyl fatty acid esters and a second liquid phase enriched with respect to said first liquid phase in tocopherols and sterols as a film in contact with said heated surface;

removing said vapor enriched in alkyl fatty acid esters from said zone and removing said film of said second liquid phase from said heated surface, said removing of said film being accomplished by mechanical agitation; and removing said second liquid phase from proximity with said zone of reduced vapor pressure to an environment of essentially ambient temperature.

In certain embodiments, the mixture is pre-heated and pre-distilled at a relatively low temperature (i.e. low relative to the moderate temperature of the packed column) as a film from a continuous heated surface and the liquid phase film is removed by gravity flow down said heated surface, for example as in a falling film evaporator.

2. Partial Stripping with Evaporator

In another aspect, this invention relates to the separation of a portion of the alkyl fatty esters from a mixture additionally comprising tocopherols and sterols, said process comprising:

applying said mixture as a film to a heated surface in proximity with a zone of reduced vapor pressure to provide a vapor phase enriched with respect to said liquid phase in alkyl fatty acid esters, said vapor phase being essentially free of tocopherols and sterols, and a liquid phase enriched with respect to said first liquid phase in tocopherols and sterols as a film in contact with said heated surface;

removing said vapor enriched in alkyl fatty acid esters from said zone and removing said film of said liquid phase from said heated surface (said removing of said film preferably being accomplished by mechanical agitation); and removing said liquid phase from proximity with said zone of reduced vapor pressure to an environment of essentially ambient temperature, (preferably wherein said liquid phase is collected in an amount of from about 30% to about 60% by weight of said mixture).

II. STEROL CRYSTALLIZATION WITH MIXED SOLVENTS OF DIFFERENTIAL POLARITY

In another aspect, this invention relates to a method of separating one or more tocopherol compounds from one or more sterol compounds comprising:

dispersing a mixture of one or more tocopherol compounds and one or more sterol compounds, said mixture being essentially free of higher fatty acid compounds, in a solvent mixture comprised of a major amount of a low polarity organic solvent, said low polarity organic solvent being selected from the group consisting of organic hydrocarbon solvents and oxygenated organic hydrocarbon solvents, and a minor amount of a high polarity organic solvent (and preferably with a minor amount of water), maintaining the resulting dispersion, preferably at a reduced temperature, to produce a liquid phase enriched in tocopherol compounds and a solid phase enriched in sterol compounds, and separating said liquid phase enriched in tocopherol compounds from said solid phase enriched in said sterol compounds.

In preferred embodiments, the process further comprises, prior to said dispersing, esterifying with an alcohol fatty compounds in a mixture comprised of fatty acids, fatty glycerides, tocopherols and sterols, distilling at least a major proportion of the fatty acid alkyl esters produced by said esterifying to produce said mixture of one or more tocopherol compounds and one or more sterol compounds.

DETAILED DESCRIPTION OF THE INVENTION

The following description will deal with the various aspects of the invention in the order presented in the outline above.

The starting material for the process of the invention is a mixture which contains fatty compounds and sterol compounds in addition to tocopherols. A major advantage of the process according to the invention is that it can be applied to various mixtures containing tocopherol and, optionally, sterol. In particular, however, it is of advantage to start out from soybean oil steamer distillate which is obtained by steam distillation of crude soybean oil as the first stage of the deodorization process. Oil deodorization is discussed in *Bailey's Industrial Oil and Fat Products*, vol. 3, pp. 127–165, (John Wiley & Sons, Inc. N.Y, N.Y., 1985), the disclosure of which is incorporated herein by reference. The distillates contain approximately 20% sterol, 8% tocopherol, 20% free fatty acids and, as its principal constituent, triglycerides (Ullmans, loc. cit.).

However, steamer distillates of other oils, for example rapeseed oil distillates, can also be processed by the process according to the invention.

The process according to the invention is by no means limited in its application to steamer distillates of vegetable oils and fats. It may also be applied with advantage to tall oil. Tall oil is, economically, one of the most important secondary products of the cellulose sulfate process used in papermaking. It is obtained by acidification of the sodium salt mixture or resinic and fatty acids formed in this process. Tall oil is a natural mixture of resinic acids of the abietic acid type, saturated and unsaturated fatty acids and fatty acid esters and an unsaponified fraction. In addition to higher alcohols and hydrocarbons, the unsaponifiable fraction also contain sterols.

Other mixtures containing tocopherol may also be worked by the process according to the invention, for example the residue obtained in the production of rapeseed oil methyl ester which also contains sterols and sterol esters.

PRE-ESTERIFICATION/ TRANSESTERIFICATION

Lower Alkanol Use and Recovery

In a first step, the free fatty acids present in the starting mixture are reacted with a lower alcohol to form fatty acid alkyl ester, more particularly fatty acid methyl ester, in order to rule out a saponification reaction with the transesterification catalyst used in the next step. In the case of mixtures with no free fatty acids, this first step may be omitted. In the following process step, transesterification, the sterol fatty acid ester is reacted to sterol and fatty acid methyl ester. The partial glycerides and triglycerides react to form glycerol and fatty acid methyl ester. The tocopherol present in the mixture does not react. In many cases, not only tocopherols, but also tocopherol esters are present in the starting mixture, for example in the soybean oil steamer distillate with 0.5% (maximum) by weight. In this step, the esters are converted into tocopherols. For the next process step, removal of the excess lower alcohol by distillation, it is of particular advantage if a short-chain alcohol, more particularly methanol, has been used in the preceding steps. In this way, exposure to high temperatures can be minimized. Before removal of the alkyl fatty acid ester by distillation, it is advisable not only to separate the glycerol formed in the transesterification step from triglycerides present, if any, but also to remove the transesterification catalyst. The catalyst is largely present in the form of alkali metal soap which could be problematical during distillation and could lead, for example, to an increase in the boiling point. A highly concentrated tocopherol/sterol mixture is obtained after removal of the fatty acid alkyl ester. The tocopherol and sterol in this mixture can be separated from one another by methods known per se, for example by crystallization.

In one preferred embodiment of the process according to the invention, the fatty acids are esterified in the presence of a strongly acidic ion exchanger, more particularly present in a fixed-bed reactor, at temperatures in the range from 60° to 100° C. and more particularly at temperatures in the range from 65° to 70° C. The distinctly smaller loss of tocopherol through its solubility in methanol than occurs in the removal of the fatty acids by distillation was both advantageous and surprising. In the esterification of the fatty acids, the ratio of the volume streams between steamer distillate and lower alcohol is between 1.1 and 1.7 and preferably 1.4. The residence time in the fixed-bed reactor is 1 to 2 hours and preferably 1.6 hours. These figures apply to the free volume actually present. In esterification, the fatty acids present in the mixture are reacted to fatty acid alkyl ester at the active centers of the strongly acidic ion exchanger. The use of polymer-supported catalysts is discussed in the *Encyclopedia of Polymer Science and Technology*, vol. 2, pp. 708–729 (John Wiley & Sons, Inc., 1985), the disclosure of which is incorporated herein by reference.

After the reaction, the excess lower alcohol, i.e. generally methanol, is removed in a phase separator. The alcohol additionally contains the predominant part of the water formed during the esterification.

The product is then transesterified in the presence of a basic catalyst, e.g. a lower alkoxide (preferably in a solution of the same lower alkanol, e.g. sodium methoxide in methanol.) Transesterification reactions are discussed in *Encyclopedia of Chemical Technology*, vol. 9, pp. 306–308 (Kirk-Othmer, eds., John Wiley & Sons, Inc., N.Y., N.Y., 1980), the disclosure of which is incorporated by reference. After the transesterification and the removal of the excess alcohol from the reaction mixture, the catalyst and any glycerol present are removed from the mixture. The catalyst is preferably neutralized before-hand by acidification with an inorganic acid (e.g. hydrochloric acid or sulfuric acid).

Pre-esterifying with Higher Alcohol

In an alternative aspect, this invention relates to a process for recovery of tocopherols from a mixture comprised of fatty acids and tocopherols wherein free fatty acids present in said mixture are pre-esterified with a higher alcohol (preferably a member selected from the group consisting of primary and secondary mono-alkanols having at least five carbon atoms) and water e.g. that produced by the pre-esterification, is removed by volatilization thereof. This process also preferably includes the steps of transesterifying fatty acid esters present in said mixture with a lower alcohol in the presence of a basic catalyst, and distilling fatty acid alkyl esters from said mixture after incapacitation (e.g. neutralization or removal) of said basic catalyst.

The process preferably employs a higher alcohol that is moderately volatile (and preferably essentially immiscible with water) such that a portion of said alcohol is distilled with said by-product water (and is preferably separated by gravity from said by-product water after condensation of said higher alcohol) and recycling higher alcohol after its distillation (and preferably after separation from by-product water). For example, a monohydric alkanol (preferably a primary alkanol or secondary alkanol), having from about five to about fourteen (preferably six to ten) carbon atoms is preferred. Examples include amyl alcohol, n-hexanol, 2-hexanol, n-heptanol, n-octanol, 2-ethylhexanol, n-nonanol, n-decanol, and 2-decanol, n-dodecanol (e.g. lauryl alcohol), n-tridecyl, and n-tetradecyl (e.g. myristyl alcohol).

In preferred embodiments, the process additionally comprises the steps of:

distilling excess lower alcohol from the product of said transesterification, washing the product of said transesterification to remove said basic catalyst and glycerol produced by said transesterification, distilling higher alcohol from the product of said transesterification as a fraction separate from said fatty acid alkyl esters. This allows for the efficient recovery and, optionally, recycling of the lower and higher alkanols.

Further, the process preferably employs as a starting material, a mixture comprised of both one or more tocopherol compounds and one or more sterol compounds (preferably comprised of one or more sterol esters that are transesterified in the pre-esterification and/or said transesterification steps) and recovering from said mixture one or more tocopherol compounds separate from one or more sterol compounds after said distillation of fatty acid alkyl esters.

A mixture of a higher alkyl alcohol and an acidic catalyst, e.g. p-toluenesulfonic acid (PTS), methanesulfonic acid, hydrochloric acid (HCl) or sulfuric acid, is introduced into a vessel. The reactants are heated and the esterification reaction is conducted at temperature sufficient to distill from the mixture water produced by the esterification of free fatty acid, preferably between 100° C. and 130° C. Higher alkyl alcohol is present in the reaction mixture during the esterification, preferably in stoichiometric excess (with respect to the free fatty acids, e.g. a ratio of about 1.5:1 to about 4:1, more typically from about 2:1 to about 2.5:1, on a molar basis) to facilitate conversion of the free fatty acids to higher alkyl fatty acid esters. The acid catalyst is present in small amounts, e.g. 0.005% to about 1.0%, typically 0.01% to about 0.2% and more typically 0.05% to 0.1%, by weight of the pre-esterified feed.

Because the higher alkyl alcohol is preferably moderately volatile (e.g. more volatile than the lower alkanols, but less volatile than the tocopherols, preferably less volatile than the alkyl fatty esters), a portion of thereof will be distilled with the water. Thus, it is preferred to continuously introduce higher alkyl alcohol into the reaction vessel and to recover the evaporated higher alkyl alcohol by the condensation. The by-product water of reaction and the higher alkyl alcohol, are preferably sufficiently immiscible to allow a gravity separation, e.g. by decantation, of water and higher alkyl alcohol.

The esterification reaction should be conducted for a time sufficient to reduce the free fatty acid concentration in the starting material to the desired degree. It is preferred to conduct the reaction to the point that there will be minimal reaction of free fatty acid with the basic catalyst used in the subsequent transesterification step. The reaction is typically conducted for a time sufficient to reduce the acid value of the product to less than one. When this value is reached, at least a portion (and preferably essentially all) of the excess higher alkyl alcohol is distilled (to recover higher alkyl alcohol in a simple distillation and reduce the potential inhibition of the subsequent transesterification reaction with a lower alcohol), typically under reduced pressure. When the reaction and subsequent distillation is completed, the reaction mixture is cooled.

The pre-esterification reaction product is then transesterified, preferably with a lower alcohol, preferably a $C_1$ to $C_4$ mono-hydric alkanol, e.g. methanol, ethanol, n-propanol, isopropanol, n-butanol, or tert-butanol. The alcohol and a catalyst, such as potassium hydroxide, sodium hydroxide or sodium methoxide, are typically added to a reaction vessel. Alcohol is present in the reaction mixture during the esterification, preferably in stoichiometric excess of fatty esters in the product. Typically, an amount of alcohol equal in mass to from about 20% to about 80%, more typically about 50% to about 60%, with respect to the mass of original tocopherol containing starting material is employed to facilitate conversion of the fatty esters (e.g. the higher alcohol fatty acid esters, glycerides, and fatty esters of sterols) to alkyl fatty acid esters. There should be essentially no water present in the reaction medium during transesterification (e.g. less than 0.1% by weight) to avoid the formation of soaps. Thus, the pre-esterification product should be dried, e.g. by air stripping or by use of an alkoxide catalyst in sufficient excess to convert any water present to methanol and a hydroxide.

Transesterification is preferably conducted at a temperature between 50° C. and 100° C. and in reaction times of 10 minutes or more, e.g. 1 to 3 hours. Typically, the vessel will be moderately pressurized (e.g. such that a reaction temperature of about 90° C. can be employed with sufficient methanol to maintain a liquid reaction phase). The reaction is conducted until the desired degree of transesterification is obtained, preferably until a major proportion (e.g. more than 50% by weight, typically at least about 90%) of the sterol fatty acid esters are transesterified to produce free sterols. The catalyst should then be neutralized with an essentially equal stoichiometric amount of acid, preferably anhydrous sulfuric acid (preferably no more than 2% by weight water). The excess alcohol (and any now free higher alcohol) should then be distilled from the mixture (e.g. in a series of simple distillation of lower alcohol followed by simple distillation of higher alcohol) prior to optional treatment with a chelating chemical (such as ascorbic acid (vitamin C), phosphoric acid, maleic acid, citric acid or tartaric acid), followed by water washing (to remove glycerol and salts), and optional nitrogen sparging and drying.

Distillation of Alkyl Fatty Acid Esters

The pre-esterification and transesterification steps performed above yield a mixture comprised of tocopherols, sterols and alkyl fatty acid esters. The alkyl fatty acid esters can be separated from the mixture as a distillate. The distillation should be accomplished in a manner such that unacceptable degradation of the tocopherols and/or sterols is avoided. Distillation is discussed in E. Hafslund, "Distillation", *Encyclopedia of Chemical Technology*, vol. 7, pp. 849–891 (Kirk-Othmer, eds. John Wiley & Sons, N.Y., 3d ed. 1979) and evaporation is discussed in F. Standiford, "Evaporation", *Encyclopedia of Chemical Technology*, vol. 9, pp. 472–493 (Kirk-Othmer, eds. John Wiley & Sons, N.Y., 3d ed. 1980), the disclosures of which are incorporated by reference.

Distillation of the alkyl fatty acid esters can be accomplished as described in U.S. Pat. No. 5,190,618 (Top et al.), the disclosure of which is incorporated by reference. In that patent, distillation equipment consists of a high heat-transfer distillation column, i.e. a high heat-transfer rate falling film distillation column, and distillate collection system. The distillation process is continuous. Alkyl esters are distilled at high vacuum at below 10 mm of Hg (1333 $N/m^3$) and at a temperature between 100° C. and 200° C. Distilled alkyl esters are collected by condensation and discharged as a by-product. The retention time of the tocopherols and sterols in the distillation column is short, so that deterioration is minimal. More than one distillation cycle may be practiced, but is clearly undesirable because of degradation of the bottoms, particularly the sterols (which tend to be particularly susceptible to heat-induced degradation).

Distillation of alkyl fatty esters is, however, preferably conducted by a employing a packed distillation column at a moderate temperature (i.e. lower than the reboiler evaporator temperature) and an evaporator at a higher temperature (i.e. higher than the temperature to which the packed column is heated) in which the liquid phase will have minimal residence time, such as in a wiped-film evaporator. This distillation is preferably accomplished by introducing a pre-heated liquid into essentially the mid-point of a packed column, removing the bottoms of the packed column to a wiped film evaporator, and removing the bottoms from the wiped film evaporator to a zone of ambient temperature. The vapor phase from the wiped film evaporator re-enters the packed column through the bottom of the column. The packed column will typically be configured to provide 5–12 theoretical stages or plates above the point of introduction and 5–12 below theoretical stages or plates below the point of introduction and will typically be operated with a temperature and pressure at the top of the column of 120° C. to 150° C. and 0.1 mbar to 3 mbar and at the bottom of the column at 180° C. to 220° C. and 3 mbar to 9 mbar, with a reflux ratio of 0.4 to 0.6 and distillate as a percentage of feed (based on weight) of 60% to 80%. This column is thus operated at a temperature that is lower than the temperature employed in the wiped film evaporator reboiler.

The wiped film evaporator will typically be operated as a reboiler for the packed column with a temperature of 200° C. to 300° C., typically at 260° C. and pressure of 50 to 90 mbar. The mechanical agitation of the film within the wiped film evaporator will ensure that the mixture of tocopherols and sterols will have a short residence time at the high temperatures employed. This will minimize degradation of the tocopherols and sterols and thus enhance the overall yields. The mechanical agitation of the film will preferably ensure that contact of any particular portion of the mixture of tocopherols and sterols with the heat exchanger surface is essentially instantaneous with removal thereof from such contact (e.g. by bringing such portion to the surface of the film in contact with the reduced pressure atmosphere maintained within the evaporator where evaporative cooling will lower the temperature of that portion of the mixture). Of course, such portion of the film can again come in contact with the surface of the heat exchanger, but will again be removed from contact therewith by the mechanical agitation. Further, the mechanical agitation will act to shorten the overall residence time in the evaporator of any particular portion of the mixture.

The distillation sequence described above will typically effect an essentially complete separation of alkyl fatty acid esters from the admixture with tocopherols and sterols. For example, the ultimate bottoms will contain less than 1%, typically less than 0.5%, of alkyl fatty acid esters. However, it may be desirable under certain circumstances to perform only a partial removal of alkyl fatty esters from such a mixture. Such a partial removal is advantageously accomplished by the process described above, but dispensing with the use of the packed column, i.e. by the use of a falling film evaporator or a wiped film evaporator. However, the heat exchanger surface will typically be heated to a lower temperature, e.g. 100° C. to 200° C. for a falling film evaporator and 150° C. to 250° C. for a wiped film evaporator, to allow for a longer residence time.

The partial stripping will be particularly advantageous if used to remove a portion of the alkyl fatty esters from a mixture wherein the weight ratio of alkyl fatty esters to total weight of tocopherols and sterols combined ranges from about 1.5:1 to about 5:1. The stripping will typically be effective in removing from about 30% to about 60% of said mixture (i.e. the esterified feed) as alkyl fatty esters in while removing only nominal amounts of tocopherols and sterols, e.g. the alkyl fatty esters will contain less than 5% by weight, typically less than 3% by weight, of tocopherols and sterols combined.

II. STEROL CRYSTALLIZATION WITH MIXED SOLVENTS OF DIFFERENTIAL POLARITY

The product of the distillation step will be enriched in tocopherols and sterols. The tocopherols and sterols can be separated from the mixture by any of a variety of means, e.g. chromatographic separation based on differential solubility and/or adsorption or other interaction with a solid phase. Preferred, however, is a method in which the mixture is dispersed in a particular solvent system which facilitates the formation of a liquid phase enriched with respect to the mixture in tocopherol compounds and a solid phase enriched with respect to the mixture in sterol compounds and then physical separation of the liquid and solid phases. This can be considered a crystallization process. Crystallization processes are discussed in the *Encyclopedia of Chemical Technology*, vol. 7, pp. 243–285 (Kirk-Othmer, eds. John Wiley & Sons, N.Y., 3d ed. 1979), the disclosure of which is incorporated herein by reference.

Of course, in the broadest sense, the mixture of tocopherols and sterols may be the product of other methods of separation of the fatty compounds normally found therewith in products of nature, e.g. by the aqueous saponification of the fatty compounds followed by extraction of the tocopherols and sterols into an organic solvent. Preferably, however, the feed for the crystallization will be the product of a distillation of fatty acid alkyl esters. Without wishing to be bound by any particular theory, unless expressly set forth otherwise, it is believed that the product of a distillation of fatty acid alkyl esters will have a composition that differs from the product of saponification and extraction in the nature and amounts of impurities and/or the identity and amounts of the tocopherols and sterols. For example, the distillation product may well have greater amounts of impurities having greater water solubility such that these impurities remained with the fatty acid soaps in the aqueous phase during the extraction of the saponification product. This difference in composition may thus cause the two different products to perform differently in a given crystallization process.

The preferred method of separating one or more tocopherol compounds from one or more sterol compounds of the mixture typically begins with dispersing a mixture of one or more tocopherol compounds and one or more sterol compounds, said mixture being essentially free of higher fatty acid compounds, in a solvent mixture comprised of a major amount of a low polarity organic solvent, a minor amount of a high polarity organic solvent, and a minor amount of water.

In the broadest sense, the high polarity solvent will be an organic solvent having a higher polarity (as measured for example by the dielectric constant of a pure liquid phase of the solvent at under ambient conditions, e.g. room temperature) than the low polarity organic solvent, and vice versa. The low polarity organic solvent will preferably have a dielectric constant of less than about 25, more preferably less than about 10, and the high polarity solvent will preferably have a dielectric constant of more than about 25, more preferably more than about 30. The dielectric constants of various organic solvents are set forth in the *Handbook of Chemistry and Physics*, pp. E-56 to E-58 (CRC Press, Inc., Cleveland, Ohio, 55th ed., 1974), the disclosure of which is incorporated herein by reference. Typically, the low polarity organic solvent will be a hydrocarbon solvent, i.e. one consisting solely of carbon and hydrogen atoms, or an oxygenated hydrocarbon solvent, e.g. one consisting solely of carbon, hydrogen, and oxygen and having less than one oxygen atom per carbon atom.

Preferred low polarity organic solvents are the higher alkanes (of sufficiently high molecular weight to form a practically handleable liquid phase, preferably straight-chain or branched-chain alkanes having from 6 to 12 carbon atoms), e.g. hexane, heptane, n-octane, iso-octane, 2,2,4-trimethylpentane, nonane, or decane; mono-ketones, e.g. acetone, 2-butanone, or 2-octanone; mono-aldehydes, e.g. acetaldehyde or propionaldehyde; mono-esters, e.g. ethyl formate or ethyl acetate; higher mono-hydric alcohols, e.g. n-propanol, iso-propanol, n-butanol, sec-butanol, n-hexanol, or 2-ethylhexanol. Preferred high polarity organic solvents are low molecular weight, oxygenated hydrocarbons, preferably the lower alkanols such as methanol or ethanol. The solvent blend will also preferably comprise a minor amount of water.

The solvent blend will be comprised of a major amount of the low polarity organic solvent, i.e. greater than 50% by weight of the solvent blend, typically at least 80% and preferably from about 90% to 99.5%, e.g. from 92.0% to 99.0%. The high polarity organic solvent will be present in a minor amount, i.e. less than 50% by weight of the solvent blend, typically less than 20% and preferably from about 0.5% to about 10%, e.g. from 1.0% to 8.0%. Water is preferably present in an amount essentially equal to the high polarity organic solvent, e.g. in a ratio of high polarity organic solvent to water of from about 5:1 to 1:5, more typically from about 3:1 to 1:3. Thus, preferred solvent blends are comprised of from about 80% to about 99% by weight of a member selected from the group consisting of higher alkanes, from about 0.5% to about 20% of methanol or ethanol, and from about 0.5% to about 5% by weight of water.

The solvent blend and mixture of tocopherols and sterols are mixed to form what is initially a substantially homogeneous liquid phase. The mixture can be heated, e.g. to the atmospheric boiling point of the solvent blend, to obtain a homogeneous liquid mixture. The ratio of solvent blend to feed mixture may vary, but will typically be from about 10:1 to about 1:1, preferably from about 5:1 to about 3:1. The resulting mixture is maintained under conditions, typically at a reduced temperature, to produce a liquid phase enriched in tocopherol compounds and a solid phase enriched in sterol compounds. The temperature of the mixture should be maintained below ambient, e.g. less than 25° C., typically from about −40° C. to 20° C., more typically from about −25° C. to about 0° C. The mixture can be cooled from the temperature of its dispersion to a reduced temperature at a variety of cooling rates, e.g. at relatively fast rates of about 80° C. per hour to about 120° C. per hour or relatively slow rates of about 2.5° C. to about 10° C. per hour.

The sterols crystallize or otherwise precipitate to form a solid phase that can be physically separated from the liquid phase, e.g. by filtering, centrifuging, or decanting. Preferably, the solid phase collected will be at least 90% (typically at least 92%) by weight sterols with less than 5% (typically less than 2%) tocopherols and the liquid phase (mother liquor) will have a ratio of tocopherols to sterols of greater than 5:1 (typically greater than 10:1 ). The mother liquor is enriched in tocopherols (with respect to the feed to the crystallization) and can be further purified by distillation to collect more highly purified tocopherols as distillate.

The following examples are intended to illustrate the invention without limiting it in any way.

EXAMPLES

Example 1

Esterification of the Fatty Acids

Part A

Soya steamer distillate having an acid value of 70 was introduced at a volumetric flow rate of 0.094 l/h together with 0.067 l/h methanol into a 0.3 m long glass column charged with catalyst, namely a strongly acidic macroporous ion exchanger resin (Lewatit K2631). The diameter of the column was 0.07 m. After a residence time of 1.6 h, the mixture was collected in a glass vessel and decanted. Subsequent concentration by evaporation to separate the methanol/water mixture from the fatty phase was carried out in vacuo. The acid value was subsequently determined at 1.3, corresponding to a conversion of 98%, i.e. the loss of tocopherol was negligible. Accordingly, the material has been deacidified for the following transesterification step.

Part B

Deodorizer distillate having an acid value of 75 was charged to a batch reactor along with 0.13% (by weight of the distillate) methanesulfonic acid and 30% (by weight of the distillate) of 2-ethylhexanol (approximately twice the amount of alcohol needed to esterify all free fatty acids in the distillate). The reaction medium was heated to 120° C. and water of reaction was removed through a reflux line at atmospheric pressure until most of the of the water of reaction had been removed (after about 3 hours), at which point the temperature of the reaction medium was raised to 135° C. and continued until an acid value of 1.2 was achieved. Vacuum was then applied and the reaction medium was heated to 150° C. to remove excess 2-ethylhexanol. A similar batch pre-esterification which employed twice the concentration of methanesulfonic acid catalyst (i.e. 0.26% by weigh of the distillate) exhibited an increased reaction rate at the beginning of the reaction, but substantially the same reaction time. A second similar batch reaction, employing 0.13% (by weight of the distillate) methanesulfonic acid catalyst and 37.5% (by weight of the distillate) reduced the reaction time to substantially the same acid value to 100 minutes.

Example 2

Transesterification of the Glycerides and Sterol Esters

Part A

The soya steamer distillate deacidified in the first step (acid value approx. 1) was contacted with methanol and the basic catalyst in a tube reactor. The reaction temperature was between 60° and 90° C. and preferably 65° C. Based on the soya steamer distillate used, 40 to 80% methanol (preferably 50 to 60%) and 0.8 to 1.5% catalyst (preferably 1%) were used. Sodium methylate was preferably used as the catalyst, although other basic catalysts, for example sodium, potassium and lithium hydroxide, etc., may also be used. The reaction time was approx. 2 h at 65° C. After the transesterification, at least 90% of the sterol esters and at least 95% of the glycerides had been reached.

Part B

A pre-esterified deodorizer distillate (pre-esterified with 2-ethylhexanol) was charged to a reactor along with 1.5% (by weight of the pre-esterified distillate) sodium methoxide and 50% (by weight of the pre-esterified distillate) of methanol. The reactor was slightly pressurized to maintain a reaction temperature of 90°. After two hours of reaction, 90% of the sterol esters present in the distillate feed were converted to free sterols. The catalyst was neutralized and the soaps were split by the addition of sulfuric acid (at 98% purity). The methanol and 2-ethylhexanol were then distilled. The recovered methanol was 98% pure with 1.5% 2-ethylhexanol and the recovered 2-ethylhexanol contained 2.6% methanol and was 01.5% pure. The bottoms were then washed with water until the bottoms exhibited a pH of about 6.

Example 3

Transesterification of the Glycerides and Sterol Esters 2.8 kg deacidified soya steamer distillate, acid value 1.9, were contacted with 1.4 kg methanol in which 192 g 30% methanolic sodium methylate had been dissolved. The mixture was heated with continuous stirring to 65° C. and was kept at that temperature for 2 h. To avoid losses of tocopherol, a nitrogen atmosphere was established.

The starting mixture contained approximately 6% free sterols, a value of 16% being determined after transesterification following removal of the methanol component. The initial glyceride content of 25% fell to 1.2%. 90% of the glycerides were monoglycerides. Triglycerides could no longer be detected.

Example 4

Removal of the Excess Methanol and Separation of Catalyst and Glycerol

After the transesterification, the excess methanol was distilled off from the reaction mixture at a temperature of 90° C./100 mbar.

The demethanolized reaction mixture contained the catalyst used mainly in the form of the alkali metal soap. To remove the catalyst from the steamer distillate, 2.2 kg demethanolized soya steamer distillate were acidified with 148 g 3% hydrochloric acid and washed with 1.1 kg water. Both phases were separated in a decanter.

Example 5

Separation of the Methyl Ester

After distillation of the methyl ester formed from the product of Example 4, a mixture containing 40 Ma % free sterols and 30 Ma % tocopherols was obtained.

Example 6

Part A

Distillation with Packed Column and Wiped Film Evaporator

A distillation apparatus comprised of a packed column and a wiped film evaporator were employed to distill methyl fatty acids ester from a mixture thereof with tocopherols and sterols (at 60.3%, 8.2%, and 9.5% by weight of the mixture, respectively). The column was packed with 3.6 meters of wire mesh packing (Montz BSH 400) and had a diameter of 316 mm (to provide eight theoretical stages above the midpoint and eight below). A line from the bottom of the column ran to a feed port of a wiped film evaporator with an evaporator surface of 1 sq. meter. A line from the top of the column ran to a condenser. A feed mixture at 138° C. was fed at 30 kg per hour to the midpoint of the column. The column was operated with a pressure and temperature at the top of the column of 136° C. and 1.6 mbar, a pressure and temperature at the bottom of the column of 200° C. and 6.6 mbar with a reflux ratio of 0.5 and a distillate per feed of 70.7%. The wiped film evaporator acted as a reboiler for the column with the reboiler temperature of 260° C. and a pressure of about 1 mbar.

The distillate was 97.0% methyl fatty acid esters and contained no measurable levels of tocopherols or sterols. The bottoms from the wiped film evaporator were 28.1% tocopherols, 31.5% sterols and 0.2% methyl fatty esters which represented a yield of tocopherols of 100% and a yield of sterols of 97.1%. This distillation apparatus could be modified by the addition of a falling film evaporator, operated at a lower temperature than the packed column, e.g. 150° C. and 1.5 mbar, to pre-distill approximately half of the methyl fatty acid esters, the bottoms of which are then fed to the packed column.

Part B
Partial Stripping with Wiped Film Evaporator

A pre-esterified, transesterified deodorizer distillate is thrice distilled as follows. The feed is introduced to a wiped film evaporator with the heat exchanger surface heated to 170° C. and with an operating pressure of about 1 mbar. The residence time is adjusted in relation to the reduced pressure to provide 13% by weight of the feed as distillate. The bottoms are once again fed to the wiped film evaporator, but the heat exchanger surface is heated to 190° C. and the residence time is adjusted in relation to the reduced pressure to provide 19% by weight of the feed as distillate. The bottoms are fed for a third time to the wiped film evaporator, but the heat exchanger is heated to 210° C. and the residence time is adjusted in relation to the reduced pressure to provide 12% by weight of the feed as distillate. Overall, about 45% by weight of the feed should be removed as distillate.

Example 7

Crystallization of Sterols

The procedure of tests to study the crystallization of sterols is as follows. We made a mixture of two parts tocopherols (T-130 from Henkel Corporation, Kankakee, Ill.) and one part sterols (Generol 100 from Henkel Corporation, Kankakee, Ill.) by adding the two in a large container and heating until consistent. We kept this mixture in an oven at approximately 70° C. to keep it liquid. We filled three 600 mL beakers with 300 grams of the solvent to be used. To the solvent, we added 75 grams of the mixture and stirred. One beaker was kept at room temperature (approximately 21° C.), one was kept in a refrigerator (–2° C.), and the third was kept in a freezer (–23° C.). These sat overnight, approximately 15 to 20 hours. After the hold time, we assembled a vacuum filtration apparatus by hooking up a 1000 mL filter flask to an aspirator vacuum source. We placed a Buchner funnel with #1 Qualitative Whatman filter paper on top of the flask and wetted the filter paper with the solvent. We filtered the solvent containing the mixture through this apparatus until all liquid had drained through the paper. While filtering, we placed a nitrogen blanket over the funnel so that the oxygen in the atmosphere did not react with the filter cake. After the filtration was complete, we placed the filter cake in a baking dish and heated in a vacuum oven overnight to remove any remaining solvent. We transferred the mother liquor to a 1000 mL round-bottom flask and stripped it with a roto-evaporator.

Example 7A—Hexane

The procedure set forth above was run employing hexane as the solvent. We noticed the formation of bright white crystals at all temperatures and a quick filter time. The procedure was twice repeated, employing hexane with methanol/water (1:1 ratio) at a 1% concentration and a 4% concentration, respectively. The procedure was twice repeated again with pure hexane, but at solvent to feed ratios of 3:1 and 2:1, respectively.

Example 7B—Heptane

The procedure set forth above was run employing heptane as the solvent. We noticed the formation of fluffy off-white crystals at all temperatures. Cold filter time was much slower.

Example 7C—Octane

The procedure set forth above was run employing octane as the solvent. We noticed the formation of fluffy off-white crystals at all temperatures. Cold filter time was much slower.

Example 7D—Trimethylpentane

The procedure set forth above was run employing trimethylpentane as the solvent. We noticed the precipitate settled on the bottom and although it began as tan, it became bright white at all temperatures.

Example 7E—Cyclohexane

The procedure set forth above was run employing cyclohexane as the solvent. We noticed a small amount of off-white cake at all temperatures and a minimal filter time.

Example 7F—Methylcyclohexane

The procedure set forth above was run employing methylcyclohexane as the solvent. We noticed no precipitate at room temperature and a small amount at colder temperatures. Filter time was minimal.

Example 7G—Methanol

The procedure set forth above was run employing methanol as the solvent. We noticed a thick slurry of a tan solution with bulky tan precipitate at all temperatures and a minimal filter time.

Example 7H—Isopropanol

The procedure set forth above was run employing isopropanol as the solvent. We noticed a very dark solution and the precipitate increased dramatically with lower temperature. Filter time was 15 to 25 minutes. The procedure was twice repeated, employing isopropanol with methanol/water (1:1 ratio) at a 4% concentration and a 8% concentration, respectively.

Example 7I—Benzl Alcohol

The procedure set forth above was run employing benzyl alcohol as the solvent. We noticed precipitate suspended in the solvent at all temperatures. The boiling point was high and the filter time was greater than 15 minutes.

Example 7J—Acetone

The procedure set forth above was run employing acetone as the solvent. We noticed large crystals settled on the bottom at all temperatures and a minimal filter time. The procedure was twice repeated, employing acetone with methanol/water (1:1 ratio) at a 4% concentration and a 8% concentration, respectively. The procedure was twice repeated again with pure acetone, but at solvent to feed ratios of 3:1 and 2:1, respectively.

Example 7K—Methyl Ethyl Ketone

The procedure set forth above was run employing methyl ethyl ketone as the solvent. We noticed opaque, white, well-defined crystals at all temperatures and a minimal filter time.

Example 7L—Formic Acid

The procedure set forth above was run employing formic acid as the solvent. We noticed an extremely dense solution at all temperatures and the tocopherol/sterol mixture would not dissolve.

Example 7M—Acetic Acid

The procedure set forth above was run employing acetic acid as the solvent. We noticed ivory precipitate at room temperature and at colder temperatures the solution was frozen.

Example 7N—Ethyl Formate

The procedure set forth above was run employing ethyl formate as the solvent. We noticed well-defined, off-white crystals at all temperatures and a minimal filter time.

Example 7O—Ethyl Acetate

The procedure set forth above was run employing ethyl acetate as the solvent. We noticed well-defined, off-white crystals at all temperatures and a minimal filter time.

Example 7P—Dichloroethane.

The procedure set forth above was run employing dichloroethane as the solvent. We noticed flaky tan crystals and the filter time was 15-25 minutes. The procedure was twice repeated, employing dichloroethane with methane/water (1:1 ratio) at a 1% concentration and a 4% concentration, respectively.

Example 7Q—Tetrahydrofuran

The procedure set forth above was run employing tetrahydrofuran as the solvent. We noticed no precipitate formed at any of the three temperatures.

Example 7R—Methyl Tetrahydrofuran

The procedure set forth above was run employing methyl tetrahydrofuran as the solvent. We noticed no precipitate formed at −23° C., so no other tests were tried.

Example 7S—Acetonitrile

The procedure set forth above was run employing acetonitrile as the solvent. We noticed the tocopherol/sterol mixture did not dissolve in the solvent at any temperature.

Example 7T—Toluene

The procedure set forth above was run employing toluene as the solvent. We noticed a small amount of precipitate in dark solution at all temperatures and a minimal filter time.

Example 7U—Cyclohexane

The procedure set forth above was run employing cyclohexane as the solvent. We noticed a large increase in precipitate at the colder temperatures.

Example 7V—Petroleum Ether

The procedure set forth above was run employing petroleum ether as the solvent. We noticed no precipitate at room temperature, a smaller amount at colder temperatures and a minimal filter time.

Example 8

Three types of crystallization processes can advantageously be used to crystallized sterols from admixture with tocopherol. The most simple process is type 1. In this process, no back flow of product is necessary. The washing liquor is combined with the mother liquor of the crystallization step. For higher purity of the mother liquor, it is suitable to lead the washing liquor back to the dissolving step like in process type 2. Compared to type 1 in this process, a larger amount of material has to be cooled and crystallized. A process following the scheme of type 3 is a two-stage process. The washed filter cake from the first crystallization step is the sterol rich product. The mother liquor is cooled to a lower temperature in a second crystallizer in order to increase the tocopherol concentration and to minimize the content of sterols. The remaining mother liquor after this second crystallization is the tocopherol rich fraction. The washing liquor from the crystals of the first stage and the crystals of the second-stage are recycled to the dissolving step. This two-step process is the most complicated because of the two crystallizers, the two solid-liquid separators and the amount of product which has to be recycled.

According to the above described processes, three types of experiments can be carried out.

Type 1: Dissolving the feed materials (boiling under reflux), cooling the mixture to the final temperature with a constant or the maximum possible cooling rate, filtering the mother liquor (if necessary the mother liquid is refilled into the vessel in order to clean it and filter it again), washing the filter cake with solvent, combining the washing liquor with the mother liquor.

Type 2: Same steps as type 1, but keeping the washing liquor and the mother liquor apart.

Type 3: Same steps as type 2, but additional cooling of the mother liquor to a lower temperature and a second filtration in order to minimize the amount of sterols in the mother liquor (two-stage-process).

A particular setup that can be employed consists of two stirred 0.5 liter vessels with condensers for the dissolving step, a unit for heating and cooling the vessels and a temperated suction funnel combined with a filter flask for the filtration step. The solution can be cooled with a constant rate between 2.5° and 10° C./h or fast cooling rate can be used. This fast rate covers a range from 80° to 120° C./h, but the average value of the cooling rate can depend strongly on the desired final temperature. A lower limit of what is considered fast can be 20° C./h.

In type 1 and 2 experiments, 60 g, and in type 3 experiments, 90 g can be used as feed. For the washing of the filter cake, 100 g of solvent can be used.

All mother and washing liquors can be stripped in a roto-evaporator until the mass of each is constant. The filter cakes can be placed in a baking dish and heated in an oven up to 75° C. until dry.

A summary of solvents, process types and conditions are shown in the following tables wherein solvent ratio (SR) is based on the mass of the solvent to the mass of the feed and the process types are as described above, but modified according to the following key:
  a: without washing the filter cake
  b: without stirring
  c: liquid trickling out of the filter cake
  d: washing the filter cake in suspension
  e: recrystallization of the filter cake.

In the following tables, the abbreviation "Meth" indicates methanol as a co-solvent at the weight % indicated. The abbreviation "syn" refers to tocopherol/sterol feed prepared by mixing commercially available tocopherol and sterol. The abbreviation "PTD" refers to a tocopherol/sterol feed prepared from a deodorizer distillate by pre-esterification, followed by transesterification, followed by distillation of the alkyl fatty acid esters. The abbreviation "ML" means that the feed was mother liquor from the immediately preceding experiment (denoted by the experiment number following the abbreviation ML). The abbreviation "Ty." refers to the experiment types described above.

TABLE 1 A
STEROL CRYSTALLIZATION WITH ACETONE

| No. | Ty. | Meth (wt. %) | Water (wt. %) | SR | Cooling Condition | Temp. (fin.) °C. | Feed Material |
|---|---|---|---|---|---|---|---|
| 1 | 1[b] | 0 | 0 | 4 | 5° C./h | 0.5 | syn |
| 2 | 1 | 0 | 0 | 4 | 5° C./h | 0.0 | syn |
| 3 | 1[b] | 0 | 0 | 4 | 5° C./h | −15.0 | syn |
| 4 | 1 | 0 | 0 | 4 | fast | −17.2 | syn |
| 5 | 1 | 0 | 0 | 4 | 5° C./h | −20.1 | syn |
| 6 | 1 | 0 | 0 | 4 | fast | −20.8 | syn |
| 7 | 1 | 0 | 0 | 3 | fast | −15.5 | syn |
| 8 | 1 | 0 | 0 | 3 | fast | −17.2 | syn |
| 9 | 1 | 0 | 2 | 4 | fast | −17.0 | syn |
| 10 | 1 | 0 | 4 | 4 | fast | −20.8 | syn |
| 11 | 1 | 0 | 7 | 4.9 | 5° C./h | 0.0 | syn |
| 12 | 1 | 2 | 0 | 4 | fast | −19.0 | syn |
| 13 | 1 | 2 | 2 | 4 | fast | −18.0 | syn |
| 14 | 1 | 2 | 2 | 4 | fast | −21.5 | syn |
| 15 | 2 | 2 | 4 | 4 | fast | −17.0 | syn |
| 16 | 1 | 4 | 0 | 4 | fast | −18.0 | syn |
| 17 | 1 | 4 | 0 | 4 | fast | −20.8 | syn |
| 18 | 1 | 4 | 2 | 4 | fast | −15.5 | syn |
| 19 | 1 | 4 | 2 | 4 | fast | −16.0 | syn |
| 20 | 2 | 4 | 2 | 3 | fast | −17.0 | syn |
| 21 | 1[b] | 4 | 4 | 4 | 5° C./h | 1.5 | syn |
| 22 | 1 | 4 | 4 | 4 | 5° C./h | 0.0 | syn |
| 23 | 1[b] | 4 | 4 | 4 | 5° C./h | −6.0 | syn |
| 24 | 1 | 4 | 4 | 4 | 5° C./h | −19.6 | syn |
| 25 | 1 | 8 | 2 | 4 | fast | −17.0 | syn |

TABLE 1 B
STEROL CRYSTALLIZATION WITH ACETONE

| No. | Ty. | Meth (wt. %) | Water (wt. %) | SR | Cooling Condition | Temp. (fin.) °C. | Feed Material |
|---|---|---|---|---|---|---|---|
| 26 | 3[a] | 0 | 0 | 4 | fast | 10.2 | syn |
| 27 | 3[a] | 0 | 0 | 4 | fast | −17.9 | ML 26 |
| 28 | 3 | 2 | 0 | 4 | fast | 0.0 | syn |
| 29 | 3[a] | 2 | 0 | 4 | fast | −15.4 | ML 28 |
| 30 | 3 | 4 | 4 | 4 | fast | 5.0 | syn |
| 31 | 3[a] | 4 | 4 | 4 | fast | −17.0 | ML 30 |
| 32 | 2 | 0 | 0 | 4 | fast | 10.0 | PTD |
| 33 | 2 | 0 | 0 | 4 | fast | −18.0 | PTD |
| 34 | 2 | 0 | 2 | 4 | fast | 10.0 | PTD |
| 35 | 2[d] | 2 | 2 | 4 | fast | 10.0 | PTD |
| 36 | 2[d] | 4 | 0 | 4 | fast | 10.0 | PTD |
| 37 | 2 | 4 | 0 | 4 | fast | −17.0 | PTD |
| 38 | 2[e] | 4 | 2 | 4 | fast | 10.0 | PTD |
| 39 | 2[e] | 4 | 2 | 4 | fast | 10.0 | PTD |
| 40 | 2 | 4 | 2 | 4 | fast | −17.0 | PTD |
| 41 | 2 | 4 | 2 | 3 | fast | −17.0 | PTD |
| 42 | 3 | 2 | 2 | 4 | fast | 9.0 | PTD |
| 43 | 3[a] | 2 | 2 | 4 | fast | −10.0 | ML 42 |
| 44 | 3 | 4 | 4 | 4 | fast | 5.0 | PTD |
| 45 | 3[a] | 4 | 4 | 4 | fast | −14.1 | ML 44 |

TABLE 2 A
STEROL CRYSTALLIZATION WITH ETHYL ACETATE

| No. | Ty. | Meth (wt. %) | Water (wt. %) | SR | Cooling Condition | Temp. (fin.) °C. | Feed Material |
|---|---|---|---|---|---|---|---|
| 46 | 1[d] | 0 | 0 | 4 | 5° C./h | 0.0 | syn |
| 47 | 1 | 0 | 0 | 4 | 5° C./h | −16.9 | syn |
| 48 | 1 | 0 | 2 | 4 | fast | 7.0 | syn |
| 49 | 1[d] | 0 | 4 | 4 | fast | −17.0 | syn |
| 50 | 1 | 2 | 0 | 4 | fast | 0.0 | syn |
| 51 | 1 | 2 | 2 | 4 | 5° C./h | 0.0 | syn |
| 52 | 1 | 2 | 2 | 4 | fast | −4.0 | syn |
| 53 | 1 | 2 | 2 | 4 | fast | −15.6 | syn |
| 54 | 1 | 2 | 2 | 4 | 5° C./h | −17.5 | syn |
| 55 | 1[d] | 2 | 2 | 3 | fast | −17.0 | syn |
| 56 | 1 | 4 | 0 | 4 | fast | −17.0 | syn |
| 57 | 1 | 4 | 0 | 4 | fast | −17.0 | syn |
| 58 | 1 | 4 | 0 | 3 | fast | −17.0 | syn |
| 59 | 2 | 4 | 2 | 4 | fast | −18.0 | syn |
| 60 | 1 | 4 | 4 | 4 | fast | −4.0 | syn |
| 61 | 1 | 4 | 4 | 4 | fast | −16.8 | syn |
| 62 | 1 | 4 | 4 | 2 | fast | −17.0 | syn |
| 63 | 2 | 6 | 4 | 4 | fast | −18.0 | syn |

TABLE 2 B
STEROL CRYSTALLIZATION WITH ETHYL ACETATE

| No. | Ty. | Meth (wt. %) | Water (wt. %) | SR | Cooling Condition | Temp. (fin.) °C. | Feed Material |
|---|---|---|---|---|---|---|---|
| 64 | 3 | 2 | 2 | 4 | fast | 0.0 | syn |
| 65 | 3[a] | 2 | 2 | 4 | fast | −18.0 | ML 64 |
| 66 | 3 | 4 | 0 | 4 | fast | 2.0 | syn |
| 67 | 3[d] | 4 | 0 | 4 | fast | −17.0 | ML 66 |
| 68 | 2 | 0 | 0 | 4 | fast | −10.0 | PTD |
| 69 | 2 | 1 | 1 | 4 | fast | −10.0 | PTD |
| 70 | 2 | 2 | 2 | 4 | fast | −10.0 | PTD |
| 71 | 2 | 4 | 0 | 4 | fast | −10.0 | PTD |
| 72 | 2[e] | 6 | 4 | 4 | fast | 10.0 | PTD |
| 73 | 2[a] | 6 | 4 | 4 | fast | 10.0 | PTD |

TABLE 2 B-continued

STEROL CRYSTALLIZATION WITH ETHYL ACETATE

| No. | Ty. | Meth (wt. %) | Water (wt. %) | SR | Cooling Condition | Temp. (fin.) °C. | Feed Material |
|---|---|---|---|---|---|---|---|
| 74 | 3 | 2 | 2 | 4 | fast | 5.0 | PTD |
| 75 | 3ª | 2 | 2 | 4 | fast | −10.0 | ML 74 |

TABLE 3 A

STEROL CRYSTALLIZATION WITH ISO-OCTANE

| No. | Ty. | Meth (wt. %) | Water (wT %) | SR | Cooling Condition | Temp. (fin.) °C. | Feed Material |
|---|---|---|---|---|---|---|---|
| 76 | 1 | 0 | 0 | 4 | 2.5/10° C./h | 10.0 | syn |
| 77 | 1 | 0 | 0 | 4 | 5° C./h | 0.0 | syn |
| 78 | 1 | 0 | 0 | 4 | fast | 0.0 | syn |
| 79 | 1 | 0 | 0 | 4 | 2.5/10° C./h | −16.7 | syn |
| 80 | 1 | 0 | 0 | 4 | 5° C./h | −17.2 | syn |
| 81 | 1 | 0 | 4 | 4 | 2.5/10° C./h | 10.0 | syn |
| 82 | 1 | 1 | 1 | 4 | fast | 0.0 | syn |
| 83 | 1 | 1.7 | 1.7 | 4 | 5° C./h | 0.0 | syn |
| 84 | 2 | 2 | 1 | 4 | fast | −18.0 | syn |
| 85 | 1 | 4 | 0 | 4 | 2.5/10° C./h | 10.0 | syn |
| 86 | 1 | 4 | 0 | 4 | fast | 0.0 | syn |
| 87 | 1 | 4 | 0 | 4 | 5° C./h | 0.0 | syn |
| 88 | 1 | 4 | 0 | 4 | 2.5/10° C./h | −16.9 | syn |
| 89 | 1 | 4 | 0 | 4 | 5° C./h | −17.7 | syn |
| 90 | 2 | 4 | 2 | 4 | fast | −18.0 | syn |
| 91 | 1 | 6 | 2 | 4 | 2.5/10° C./h | 10.0 | syn |
| 92 | 1 | 6 | 2 | 4 | 5° C./h | 0. | syn |
| 93 | 1 | 6 | 2 | 4 | fast | 0.0 | syn |

TABLE 3 B

STEROL CRYSTALLIZATION WITH ISO-OCTANE

| No. | Ty. | Meth (wt. %) | Water (wt. %) | SR | Cooling Condition | Temp. (fin.) °C. | Feed Material |
|---|---|---|---|---|---|---|---|
| 94 | 3 | 4 | 0 | 4 | fast | 10.0 | syn |
| 95 | 3ª | 4 | 0 | 4 | fast | −16.0 | ML 94 |
| 96 | 3 | 6 | 2 | 4 | fast | 10.0 | syn |
| 97 | 3ª | 6 | 1 | 4 | fast | −17.0 | ML 96 |
| 98 | 2 | 2 | 0 | 4 | fast | 0.0 | PTD |
| 99 | 2 | 4 | 0 | 4 | fast | 0.0 | PTD |
| 100 | 2ª | 4 | 0 | 4 | fast | −17.0 | PTD |
| 101 | 2 | 6 | 2 | 4 | fast | 0.0 | PTD |
| 102 | 2 | 6 | 2 | 4 | fast | 0.0 | PTD |
| 103 | 2 | 6 | 2 | 4 | fast | 0.0 | PTD |
| 104 | 2ª | 6 | 2 | 4 | fast | −13.0 | PTD |
| 105 | 3 | 4 | 2 | 4 | fast | −10.0 | PTD |
| 106 | 3ª | 4 | 2 | 4 | fast | −17.0 | ML 105 |
| 107 | 3 | 6 | 2 | 4 | fast | 9.0 | PTD |

TABLE 3 B-continued

STEROL CRYSTALLIZATION WITH ISO-OCTANE

| No. | Ty. | Meth (wt. %) | Water (wt. %) | SR | Cooling Condition | Temp. (fin.) °C. | Feed Material |
|---|---|---|---|---|---|---|---|
| 108 | 3ª | 6 | 2 | 4 | fast | −13.0 | ML 107 |

What is claimed is:

1. An evaporative process for the separation of fatty acid lower alkyl esters from a mixture additionally comprising tocopherols and sterols, said process comprising:

introducing said mixture into a moderately heated zone of elevated temperature and reduced pressure, said zone containing multiple packing elements in an essentially continuous bed, said elevated temperature and reduced pressure being effective to provide within said continuous bed a first vapor phase enriched with respect to said mixture in alkyl fatty acid esters and a first liquid phase enriched with respect to said mixture in tocopherols and sterols;

removing liquid phase enriched in tocopherols and sterols from said continuous bed at a point gravitationally below the point of introduction of said mixture into said heated zone;

removing vapor phase enriched in alkyl fatty acid esters from said continuous bed at a point gravitationally above the point of introduction of said mixture into said heated zone;

applying said liquid phase enriched in tocopherols and sterols as a film to a highly heated surface in proximity with a zone of reduced vapor pressure to provide a second vapor phase enriched with respect to said liquid phase in alkyl fatty acid esters and a second liquid phase enriched with respect to said first liquid phase in tocopherols and sterols as a film in contact with said heated surface;

removing said vapor enriched in alkyl fatty acid esters from said zone and removing said film of said second liquid phase from said heated surface, said removing of said film being accomplished by mechanical agitation; and removing said second liquid phase from proximity with said zone of reduced vapor pressure to an environment of essentially ambient temperature.

2. A process of claim 1 wherein the mixture, prior to introduction into said packed column, is pre-heated and pre-distilled as a film from a continuous heated surface, said heated surface being at a temperature lower than said packed column, and wherein said film on said continuous surface is removed by gravity flow down said heated surface.

3. A process as claimed in claim 1 said mixture is introduced as a pre-heated liquid into essentially the mid-point of a packed column, the bottoms of the packed column are removed to a wiped film evaporator, and the bottoms from the wiped film evaporator are removed to a zone of ambient temperature.

4. A process as claimed in claim 3 wherein the vapor phase from the wiped film evaporator re-enters the packed column through the bottom of the column.

5. A process as claimed in claim 3 wherein the packed column is configured to provide 5 to 12 theoretical stages above the point of introduction of said mixture and 5 to 12 theoretical stages below the point of introduction of said mixture.

6. A process as claimed in claim 3 wherein the packed column is operated with a temperature and pressure at the top of the column of 120° C. to 150° C. and 0.1 mbar to 3 mbar and at the bottom of the column of 180° C. to 220° C. and 3 mbar to 9 mbar.

7. A process as claimed in claim 3 wherein said packed column is operated with a reflux ratio of 0.4 to 0.6.

8. A process as claimed in claim 3 wherein said packed column is operated with distillate as a percentage of feed of 60% to 80% by weight.

9. A process as claimed in claim 3 wherein the wiped film evaporator is operated with a temperature of 200° C. to 300° C. and pressure of 50 to 90 mbar.

10. A process as claimed in claim 1 wherein said second liquid phase contains less than 1% by weight of alkyl fatty acid esters.

11. A process for the separation of a portion of the alkyl fatty esters from a mixture additionally comprising tocopherols and sterols, said process comprising:

applying said mixture as a film to a heated surface in proximity with a zone of reduced vapor pressure to provide a vapor phase enriched with respect to said liquid phase in alkyl fatty acid esters, said vapor phase being essentially free of tocopherols and sterols, and a liquid phase enriched with respect to said first liquid phase in tocopherols and sterols as a film in contact with said heated surface;

removing said vapor enriched in alkyl fatty acid esters from said zone and removing said film of said liquid phase from said heated surface; and removing said liquid phase from proximity with said zone of reduced vapor pressure to an environment of essentially ambient temperature, wherein said liquid phase is collected in an amount of from about 30% to about 60% by weight of said mixture.

12. A process as claimed in claim 11 wherein said removing of said film is accomplished by mechanical agitation.

13. A process as claimed in claim 11 wherein said applying and removing are accomplished by use of a falling film evaporator.

14. A process as claimed in claim 13 wherein said heated surface is at a temperature of from 100° C. to 200° C.

15. A process as claimed in claim 11 wherein said applying and removing are accomplished by use of a wiped film evaporator.

16. A process as claimed in claim 15 wherein said heated surface is at a temperature of from 150° C. to 250° C.

17. A process as claimed in claim 11 wherein the weight ratio of alkyl fatty esters to total weight of tocopherols and sterols combined in said mixture applied to said heated surface ranges from about 1.5:1 to about 5:1.

18. A process as claimed in claim 11 wherein said vapor enriched in alkyl fatty esters contains less than 5% by weight of tocopherols and sterols combined.

* * * * *